(12) United States Patent
Aguilar (10) Patent No.: US 10,507,098 B2
(45) Date of Patent: Dec. 17, 2019

(54) 3D PRINTER

(71) Applicant: Mariela Aguilar, San Jose, CA (US)

(72) Inventor: Mariela Aguilar, San Jose, CA (US)

(73) Assignee: Bao Tran, Saratoga, CA (US)

( * ) Notice: Subject to any disclaimer, the term of this patent is extended or adjusted under 35 U.S.C. 154(b) by 47 days.

(21) Appl. No.: 15/947,791

(22) Filed: Apr. 7, 2018

(65) Prior Publication Data
US 2018/0221135 A1 Aug. 9, 2018

Related U.S. Application Data

(63) Continuation of application No. 14/746,631, filed on Jun. 22, 2015, now Pat. No. 9,968,437.

(51) Int. Cl.
| | | |
|---|---|---|
| *A61F 2/10* | (2006.01) | |
| *A61L 27/60* | (2006.01) | |
| *A61L 27/24* | (2006.01) | |
| *A61L 27/38* | (2006.01) | |
| *A61L 27/48* | (2006.01) | |
| *A61L 27/54* | (2006.01) | |
| *B33Y 10/00* | (2015.01) | |
| *A61F 2/28* | (2006.01) | |
| *A61F 2/30* | (2006.01) | |
| *B33Y 80/00* | (2015.01) | |
| *G06T 7/73* | (2017.01) | |

(52) U.S. Cl.
CPC .............. *A61F 2/105* (2013.01); *A61L 27/24* (2013.01); *A61L 27/38* (2013.01); *A61L 27/3834* (2013.01); *A61L 27/48* (2013.01); *A61L 27/54* (2013.01); *A61L 27/60* (2013.01); *B33Y 10/00* (2014.12); *A61F 2/28* (2013.01); *A61F 2002/30985* (2013.01); *A61F 2210/0004* (2013.01); *A61F 2240/002* (2013.01); *A61F 2240/004* (2013.01); *A61L 2300/414* (2013.01); *B33Y 80/00* (2014.12); *G06T 7/74* (2017.01)

(58) Field of Classification Search
CPC ................ A61F 2/105; A61F 2090/365; A61F 2002/30985; B33Y 30/00; B33Y 10/00; B33Y 80/00; A61B 2034/2065; A61B 2090/364; G06T 7/74
See application file for complete search history.

(56) References Cited

U.S. PATENT DOCUMENTS

2014/0256695 A1* 9/2014 Nguyen ................. A61L 27/26
514/180
2015/0139960 A1* 5/2015 Tumey ................... A61K 35/36
424/93.7

OTHER PUBLICATIONS https://www.youtube.com/watch?v=2t_3znIPVyQ Sep. 15, 2014 (Year: 2014).*

(Continued)

*Primary Examiner* — Brian E Pellegrino
*Assistant Examiner* — Rebecca Lynee Zimmerman
(74) *Attorney, Agent, or Firm* — Tran & Associates (57) ABSTRACT

A method of reproducing a biological object includes 3D-imaging the object and generating a mold using a 3D printer; obtaining cells from a donor site on the object; preparing a live cell suspension using the cells from the donor site; forming a scaffold in the mold with collagen and seeding the scaffold with live cells, growing the cells in the mold and curing the collagen; and surgically implanting the object into a living subject, where the cells continue to live in the living subject.

9 Claims, 4 Drawing Sheets

(56) References Cited

OTHER PUBLICATIONS https://www.dezeen.com/2013/12/23/3d-printing-biopen-draws-bone-repairs-with-stem-cells/ Dec. 23, 2013 (Year: 2013).*
https://3dprint.com/64485/pioneering-3d-printing-tissue/ May 12, 2015 (Year: 2015).*

* cited by examiner

| |
|---|
| Preparing 300 a wound region (e.g., NPWT—debridement/irrigation, dressings to manage exudate, reduce/eliminate infection, create vascularized granular bed of tissue). |
| Imaging 302 the wound using the pen imaging system and model a graft in 3D from the wound image. |
| Obtaining 304 dermal cells from donor site (estimating a ratio, such as estimating a 1:5 ratio). |
| Preparing 306 a live cell suspension using the dermal cells from the donor site and insert the cartridge with the live cell suspension into the pne. |
| 3D printing 308 onto the wound region an acellular dermal matrix (ADM) scaffold with collagen and hyaluronic acid seeded with live cells processed from the autologous graft. |
| Printing the ADM scaffold 310, securing with sutures and covering with a suitable bandage. |
| Optionally an electrical field is applied to the wound region during printing. Other options include pressure-relieving devices, hyperbaric or topically applied oxygen, whirlpool/pulsed lavage, negative pressure therapy, ultrasound, topical antibiotics, and cytokine growth factors. Electrical stimulation (ES) can provide therapeutic levels of electrical current may be delivered into the wound tissue from an external source. |

| |
|---|
| Place Deionized Water in the vessel where batch has to be manufactured |
| Add item Carbomer, Allantoin, Dipotassium Glycerrhizate, and Disodium EDTA mixing and mix for 10-20 minutes |
| Add all remaining items in Table 1 except for Tiethanolamine to the batch one by one |
| Mix the batch for 5-10 minutes and add Tiethanolamine with mixing |
| Mix the batch for 5-10 minutes and take collagen sample for QC |
| Phosphorylate the collagen and 3D print the collagen onto the damaged skin |

3D PRINTER

BACKGROUND

Additive manufacturing, otherwise known as three-dimensional (3D) printing, is driving major innovations in many areas, such as engineering, manufacturing, art, education and medicine. Recent advances have enabled 3D printing of biocompatible materials, cells and supporting components into complex 3D functional living tissues. 3D bioprinting is being applied to regenerative medicine to address the need for tissues and organs suitable for transplantation.

SUMMARY

A method of healing a skin wound includes
  imaging the skin wound using an imager including a supply cartridge;
  obtaining dermal cells from a donor site; preparing a live cell suspension using the dermal cells from the donor site and insert the supply cartridge with the live cell suspension into the pen;
  3D printing onto the wound region an acellular dermal matrix (ADM) scaffold with collagen and seeded with live cells processed from the autologous graft; and
  securing with sutures and covering with a suitable bandage.

In another aspect, a process for printing an object includes:
  providing a 3D printing engine in a pen body with a camera;
  imaging a target area with the camera; and
  injecting materials onto the target area based on the imaged target area.

In another aspect, a process for printing an object includes:
  providing a 3D printing engine in a pen body with a camera;
  imaging a skin area with the camera; and
  injecting materials onto the skin area based on the imaged target area to heal the skin.

In another aspect, a process for printing an object includes:
  providing a 3D printing engine;
  injecting cell with collagen and hyaluronic acid onto the target area based on the imaged target area; and
  photocrosslinking the hyaluronic at each deposition to cure a layer of the object at a time.

In a further aspect, a process for printing a biological object, comprising:
  forming a hyaluronic acid interpenetrating network (HA IPN); and
  3D printing a substrate with the HA IPN.

The HA IPN can be formed using one of: physical or chemical means. The physical means comprise ionic, stereocomplex, or thermal techniques. The chemical cross-linking comprises polymerization using UV irradiation or wet chemical techniques.

In yet another aspect, a method of healing a skin wound, includes
  imaging the skin wound using an imager including a supply cartridge;
  obtaining dermal cells from a donor site;
  preparing a live cell suspension using the dermal cells from the donor site and insert the supply cartridge with the live cell suspension into the pen;
  3D printing onto the wound region an acellular dermal matrix (ADM) scaffold with collagen and seeded with live cells processed from the autologous graft; and
  securing with sutures and covering with a suitable bandage.

Implementations may include auto-grafting a three-dimensional irregularly-shaped skin graft product. The method may include printing a quantity of harvested skin cells. The method may include imaging the wound, wherein the harvested skin cells comprises a quantity of living skin cells from a patient with an imaged wound and a quantity of material not from the patient with the imaged wound.

In yet another aspect, a wound healing composition includes deionized water; carbomer, allantoin, dipotassium glycerrhizate, disodium EDTA (ethylenediaminetetraacetic acid), collagen, tiethanolamine; and PX3 Phosphorus (Othophosphoric Acid) for phosphorylating the collagen.

In another aspect, a process for forming the wound healing solution is also disclosed. Deionized Water is placed in a vessel where batch has to be manufactured. Next, Carbomer, Allantoin, Dipotassium Glycerrhizate, and Disodium EDTA are added and mixed for 10-20 minutes. The remaining items in Table 1, except for Tiethanolamine, are added to the batch one by one. The batch is mixed for 5-10 minutes and Tiethanolamine is added with mixing. The batch is mixed for 5-10 minutes and the resulting collagen sample(s) can be taken for QC.

In another aspect, a process for forming a wound healing composition includes: depositing deionized water in a vessel; adding carbomer, allantoin, dipotassium glycerrhizate, and disodium EDTA (ethylenediaminetetraacetic acid) one at a time into a batch and mixing the batch for a predetermined period; adding collagen and mixing the batch; adding tiethanolamine and mixing the batch; and phosphorylating the collagen with PX3 Phosphorus (Othophosphoric Acid).

In yet another aspect, a method of reproducing a biological object by 3D-imaging the object and generating a mold using a 3D printer; obtaining cells from a donor site on the object; preparing a live cell suspension using the cells from the donor site; forming a scaffold with collagen and hyaluronic acid and seeding the scaffold with live cells; and surgically implanting the object into a living subject, where the cells continue to live in the living subject.

BRIEF DESCRIPTION OF THE DRAWINGS

FIG. 2 illustrates an embodiment of the 3D printer pen, while

DESCRIPTION

Figure 1:
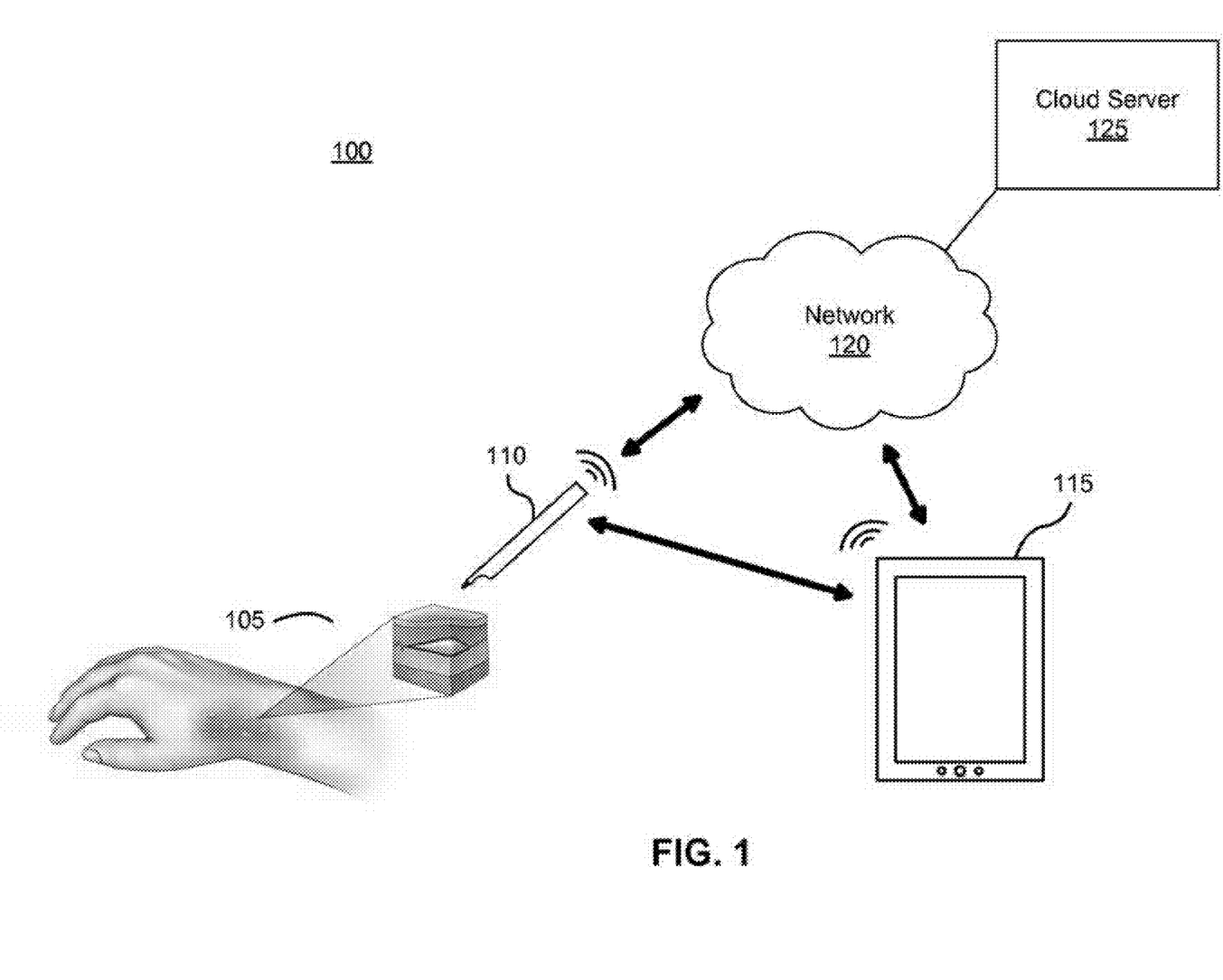
FIG. 1 illustrates an embodiment of a pen-based biological printing system.

FIG. 1 illustrates an embodiment of a pen-based biological printing system 100. The pen-based system comprises a tissue or organ target surface 105, a 3D printer pen 110, a computing device 115, a network 120, and a cloud server 125. In alternative embodiments, different or additional devices may be present such as, for example, additional 3D printer pens 110, biological surfaces 105, and computing devices 115 (or one or more device may be absent). As shown in FIG. 1, the pen system repairs burned skin on a hand. However, other applications are contemplated. In one embodiment, the biological surface 105 can be skin or can be heart, ear, lung, or any suitable organs. Typically, the pen deposits cells in a support scaffold such as hyaluronic acid or collagen, for example. Examples of contents of 3D printer cell dispensed include, autologous fibroblasts, keratinocytes, ECM proteins, growth factors (GF s), cytokines. Examples of contents of 3D printer cell dispensed are, e.g., GF, insulin, PDGF, eNOS. Examples of contents of 3D printer cell dispensed are lyophyllized amniotic membrane. The result is a cultured graft preferably comprising bovine collagen, hyaluronic acid, media, growth factors (GF s), etc.

Although not required, cells can typically be printed in the form of a "cell composition" that contains a liquid carrier for the cells. The cell composition can be in the form of a suspension, solution, or any suitable form. Examples of suitable liquid carriers include, but are not limited to, water, ionic buffer solutions (e.g., phosphate buffer solution, citrate buffer solution, etc.), liquid media (e.g., modified Eagle's medium ("MEM"), Hanks' Balanced Salts, etc.), and so forth. For instance, the use of a liquid carrier in the cell composition can ensure adequate hydration and minimize evaporation of the cells after printing. Various mechanisms may be employed to facilitate the survival of the cells during and/or after printing. Specifically, compounds may be utilized that "support" the printed cells by providing hydration, nutrients, and/or structural support. These compounds may be applied to the substrate using conventional techniques, such as manually, in a wash or bath, through vapor deposition (e.g., physical or chemical-vapor deposition), etc. These compounds may also be combined with the cell composition before and/or during printing, or may be printed or otherwise applied to the substrate (e.g., coated) as a separate layer beneath, above, and/or between cell layers. For example, one such support compound is a gel having a viscosity that is low enough under the printing conditions to pass through the nozzle of the printer head, and that can gel to a stable shape during and/or after printing. Such viscosities are typically within the range of from about 0.5 to about 50 centipoise, in some embodiments from about 1 to about 20 centipoise, and in some embodiments, from about 1 to about 10 centipoise. Some examples of suitable gels that may be used in the present invention include, but are not limited to, agars, collagen, hydrogels, etc. One example of a collagen gel for facilitating cell growth is described in Collagen As a Substrate for Cell Growth and Differentiation, Methods in Enzymology, Strom and Michalopoulous, Vol. 82. 544-555 (1982) (T. Boland at para 50).

Besides gels, other support compounds may also be utilized in the present invention. Extracellular matrix analogs, for example, may be combined with support gels to optimize or functionalize the gel. One or more growth factors may also be introduced in the printed cell arrays. For example, slow release microspheres that contain one or more growth factors in various concentrations and sequences may be combined with the cell composition to accelerate and direct the cell fusion process. Other suitable support compounds might include those that aid in avoiding apoptosis and necrosis of the developing structures. For example, survival factors (e.g., basic fibroblast growth factor) may be added. In addition, transient genetic modifications of cells having antiapoptotic (e.g., bcl-2 and telomerase) and/or blocking pathways may be included in cell aggregates to be printed according to the invention. Adhesives may also be utilized to assist in the survival of the cells after printing. For instance, soft tissue adhesives, such a cyanoacrylate esters, fibrin sealant, and/or gelatin-resorcinol-formaldehyde glues, may be utilized to inhibit nascent constructs from being washed off or moved following printing of a layer. In addition, adhesives, such as arginine-glycine-aspartic acid ligands, may enhance the adhesion of cells to a gelling polymer or other support compound. In addition, extracellular proteins, extracellular protein analogs, etc., may also be utilized (T. Boland at para 55).

Besides two-dimensional arrays, three-dimensional arrays may also be formed. Three-dimensional cell arrays are commonly used in tissue engineering and biotechnology for in-vitro and in-vivo cell culturing. In general, a three-dimensional array is one which includes two or more layers separately applied to a substrate, with subsequent layers applied to the top surface of previous layers. The layers can, in one embodiment, fuse or otherwise combine following application or, alternatively, remain substantially separate and divided following application to the substrate. Three-dimensional arrays may be formed in a variety of ways in accordance with the present invention. For example, in one embodiment, three-dimensional arrays may be formed by printing multiple layers onto the substrate. (T. Boland at para 60).

The thickness of a printed layer (e.g., cell layer, support layer, etc.) may generally vary depending on the desired application. For example, in some embodiments, the thickness of a layer containing cells is from about 2 micrometers to about 3 millimeters, and in some embodiments, from about 20 micrometers to about 100 micrometers. Further, as indicated above, support compounds, such as gels, are often used to facilitate the survival of printed cells. The present inventors have discovered that the development of a cellular assembly may be increased when the thickness of the support layer(s) (e.g., between cells) is approximately the same as the size of the cells deposited adjacent to the support compound (T. Boland at para 61).

When printing certain types of two-dimensional or three-dimensional arrays, it is sometimes desired that any subsequent cell growth is substantially limited to a predefined region. Thus, to inhibit cell growth outside of this predefined region, compounds may be printed or otherwise applied to the substrate that inhibit cell growth and thus form a boundary for the printed pattern. Some examples of suitable compounds for this purpose include, but are not limited to, agarose, poly(isopropyl N-polyacrylamide) gels, and so forth. In one embodiment, for instance, this "boundary technique" may be employed to form a multi-layered, three-dimensional tube of cells, such as blood vessels. For example, a cell suspension may be mixed with a first gel ("Gel A") in one nozzle, while a second gel ("Gel B") is loaded into another nozzle. Gel A induces cell attachment and growth, while Gel B inhibits cell growth. To form a tube, Gel A and the cell suspension are printed in a circular pattern with a diameter and width corresponding to the diameter and wall thickness of the tube, e.g., from about 3 to about 10 millimeters in diameter and from about 0.5 to about 3 millimeters in wall thickness. The inner and outer patterns are lined by Gel B defining the borders of the cell growth. For example, a syringe containing Gel A and "CHO" cells and a syringe containing Gel B may be connected to the nozzle. Gel B is printed first and allowed to cool for about 1 to 5 minutes. Gel A and CHO cells are then printed on the agarose substrate. This process may be repeated for each layer. (T. Boland at para 62).

The printing of tissues can be done with an appropriate combination of cell and support material, or two or three or more different cell types typically found in a common tissue, preferably along with appropriate support compound or compounds, and optionally but preferably with one or more appropriate growth factors. Cells, support compounds, and growth factors may be printed from separate nozzles or through the same nozzle in a common composition, depending upon the particular tissue (or tissue substitute) being formed. Printing may be simultaneous, sequential, or any combination thereof. Some of the ingredients may be printed in the form of a first pattern (e.g., an erodable or degredable support material), and some of the ingredients may be printed in the form of a second pattern (e.g., cells in a pattern different from the support, or two different cell types in a different pattern). Again the particular combination and manner of printing will depend upon the particular tissue.

The 3D printer pen 110 is an electronic device that digitally prints tissue or organ surface 105 (e.g., with writing gestures and/or control inputs). The 3D printer pen 110 is communicatively coupled to the computing device 115 either directly or via the network 120. The captured printing gestures and/or control inputs may be transferred from the 3D printer pen 110 to the computing device 115 (e.g., either in real time or at a later time) for use with one or more applications executing on the computing device 115. Furthermore, digital data and/or control inputs may be communicated from the computing device 115 to the 3D printer pen 110 (either in real time or as an offline process) for use with an application executing on the smart pen 110. Commands may similarly be communicated from the 3D printer pen 110 to the computing device 115 for use with an application executing on the computing device 115. The cloud server 125 provides remote storage and/or application services that can be utilized by the 3D printer pen 110 and/or the computing device 115. The pen-based 3D printing system 100 thus enables a wide variety of applications that combine user interactions for tissue/organ printing.

In one embodiment, the 3D printer pen 110 comprises a biofabrication instrument (e.g., an ink-based tissue printing pen, a stylus device without cells, a stylus device that deposits cells, a pencil, or other writing apparatus) with embedded computing components and various input/output functionalities. A user may write with the 3D printer pen 110 on the biological surface 105 as the user would with a conventional pen. During the operation, the 3D printer pen 110 deposits the biological materials and also digitally captures the writing gestures made on the biological surface 105 and stores electronic representations of the writing gestures. The captured writing gestures have both spatial components and a time component. In one embodiment, the 3D printer pen 110 captures position samples (i.e., coordinate information) of the 3D printer pen 110 with respect to the biological surface 105 at various sample times and stores the captured position information together with the timing information of each sample. The captured writing gestures may furthermore include identifying information associated with the particular biological surface 105 such as, for example, identifying information of a tissue (skin/ear/ . . . ) so as to distinguish between data captured with different biological surfaces 105. In another embodiment, the 3D printer pen 110 also captures other attributes of the writing gestures chosen by the user. For example, material to be deposited may be selected by tapping a printed icon on a page or, selecting an icon on a computer display, etc. The biological ink information (material type, line width, line style, etc.) may also be encoded in the captured data.

In an embodiment, the computing device 115 additionally captures contextual data while the 3D printer pen 110 deposits biological materials. In an alternative embodiment, written gestures may instead be captured by biological surface 105 instead of, or in addition to, being captured by the smart pen 110. The contextual data may include audio and/or video from an audio/visual source (e. g., the surrounding room). Contextual data may also include, for example, user interactions with the computing device 115 (e.g. documents, web pages, emails, and other concurrently viewed content), information gathered by the computing device 115 (e.g., geospatial location), and synchronization information (e.g., cue points) associated with time-based content (e.g., audio or video) being viewed or recorded on the computing device 115. The computing device 115 stores the contextual data synchronized in time with the captured writing gestures (i.e., the relative timing information between the captured written gestures and contextual data is preserved). In an alternate embodiment, the 3D printer pen 110 or a combination of a 3D printer pen 110 and a computing device 115 captures contextual data. Furthermore, in an alternate embodiment, some or all of the contextual data can be stored on the 3D printer pen 110 instead of, or in addition to, being stored on the computing device 115.

In one embodiment, the 3D printer pen 110 can automatically recognize/detect biological objects (such as wound outlines) or other pre-existing content on the biological surface 105. In one embodiment, the 3D printer pen 110 directly recognizes the biological object (e.g., by performing image processing and recognition). In another embodiment, the smart pen recognizes positional information of the 3D printer pen 110 and determines what pre-content is being interacted by correlating the captured positional information with known positional information of the pre-existing content. In order to enable communication between the 3D printer pen 110 and the computing device 115, the 3D printer pen 110 and the computing device 115 may establish a "pairing" with each other. The pairing allows the devices to recognize each other and to authorize data transfer between the two devices. Once paired, data and/or control signals may be transmitted between the 3D printer pen 110 and the computing device 115 through wired or wireless means. In one embodiment, both the 3D printer pen 110 and the computing device 115 carry a TCP/IP network stack linked to their respective network adapters. The devices 110, 115 thus support communication using direct (TCP) and broadcast (UDP) sockets with applications executing on each of the 3D printer pen 110 and the computing device 115 able to use these sockets to communicate.

The network 120 enables communication between the smart pen 110, the computing device 115, and the cloud server 125. The network 120 enables the 3D printer pen 110 to, for example, transfer captured contextual data between the smart pen 110, the computing device 115, and/or the cloud server 125, communicate control signals between the smart pen 110, the computing device 115, and/or cloud server 125, and/or communicate various other data signals between the smart pen 110, the computing device 115, and/or cloud server 125 to enable various applications. The network 120 may include wireless communication protocols such as, for example, Bluetooth, WiFi, WiMax, cellular networks, infrared communication, acoustic communication, or custom protocols, and/or may include wired communication protocols such as USB or Ethernet. Alternatively, or in addition, the 3D printer pen 110 and computing device 115 may communicate directly via a wired or wireless connection without requiring the network 120.

The cloud server 125 comprises a remote computing system coupled to the 3D printer pen 110 and/or the computing device 115 via the network 120. For example, in one embodiment, the cloud server 125 provides remote storage for data captured by the 3D printer pen 110 and/or the computing device 115. Furthermore, data stored on the cloud server 125 can be accessed and used by the 3D printer pen 110 and/or the computing device 115 in the context of various applications.

Figure 2:
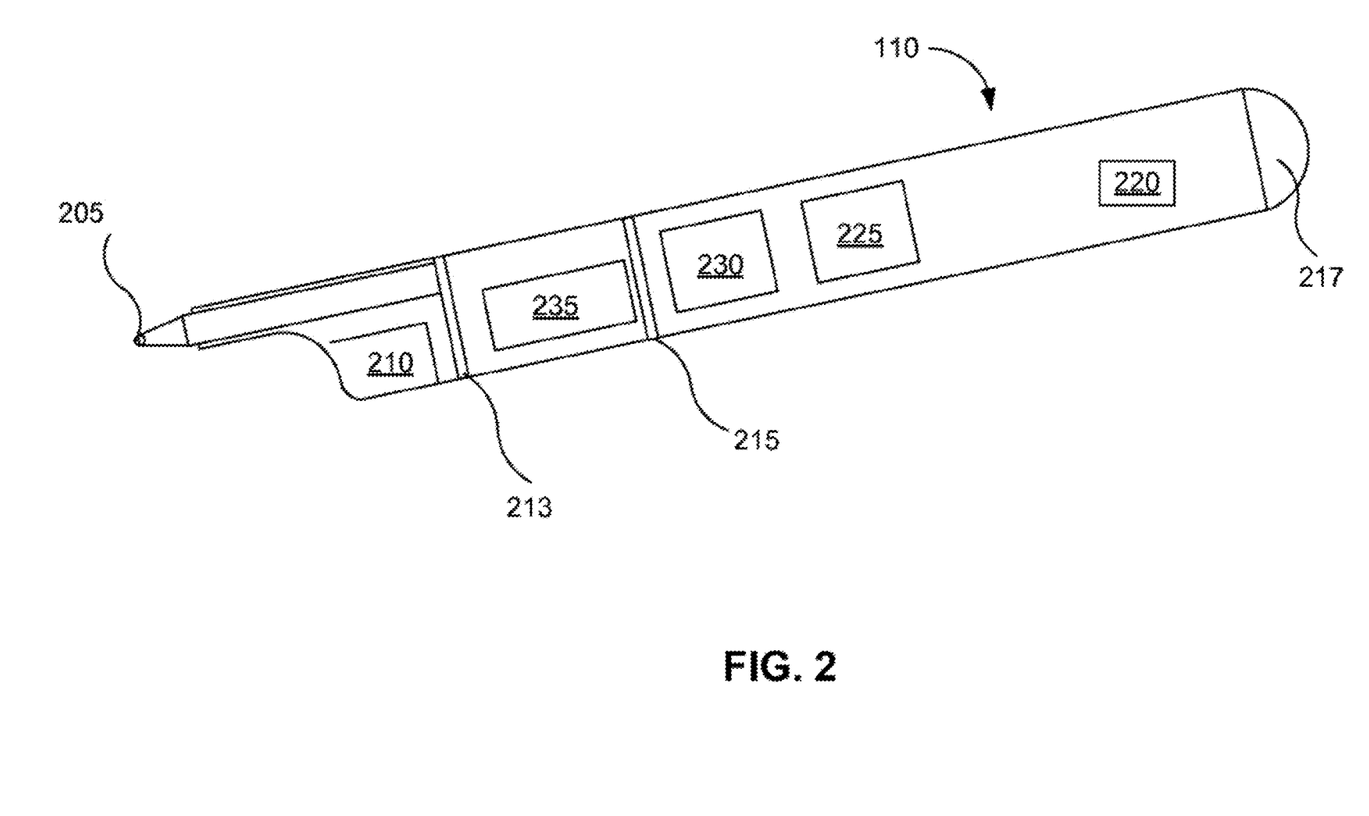

FIG. 2 illustrates an embodiment of the 3D printer pen 110. In the illustrated embodiment, the 3D printer pen 110 comprises a deposit nozzle 205, an imaging system 210, a pen actuation sensor 213, a power state mechanism 215, a tip 217, an I/O port 220, a processor 225, an onboard memory 230, and a battery 235. Other optional components of the 3D printer pen 110 are omitted from FIG. 2 for clarity of description including, for example, status indicator lights, buttons, one or more microphones, a speaker, an audio jack, and a display. In alternative embodiments, the 3D printer pen 110 may have fewer, additional, duplicate, or different components than those illustrated in FIG. 2.

Figure 3:
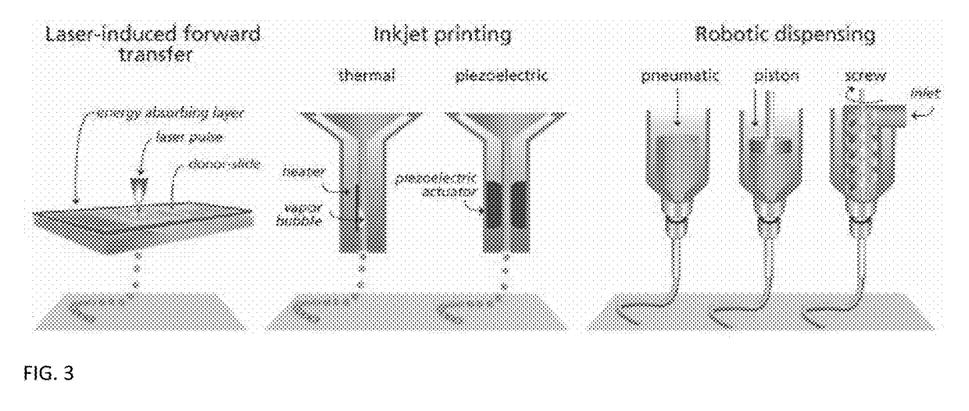
FIG. 3 shows exemplary 3D biological printing engines in the 3D printer pen.

The deposit nozzle 205 comprises any suitable 3D printing nozzles as shown in FIG. 3, including inkjet, microextrusion, or laser printers. Thermal inkjet printers electrically heat the printhead to produce air-pressure pulses that force droplets from the nozzle, whereas acoustic printers use pulses formed by piezoelectric or ultrasound pressure. Microextrusion printers use pneumatic or mechanical (piston or screw) dispensing systems to extrude continuous beads of material and/or cells. Laser-assisted printers use lasers focused on an absorbing substrate to generate pressures that propel cell-containing materials onto a collector substrate. In one embodiment, 3D printing materials such as hydrogels with suspended cells are generally inserted in disposable plastic syringes in the pen and dispensed, either pneumatic, piston- or screw-driven, in the pen. Rather than single droplets, robotic dispensing yields larger hydrogel strands. In order to maintain the shape of the constructs after printing, hydrogels with higher viscosities are often used. Piston-driven deposition generally provides more direct control over the flow of the hydrogel from the nozzle, due to the delay of the compressed gas volume in the pneumatic systems. Screw-based systems may give more spatial control and are beneficial for the dispensing of hydrogels with higher viscosities.

In one embodiment the deposit nozzle 205 is driven by a syringe-type dispenser. A syringe driver or syringe pump is a small infusion pump (some include infuse and withdraw capability), used to gradually administer small amounts of fluid (with or without medication) to a predetermined region. Syringe pumps use a series of sensors and a motor driven plunger head to infuse liquid at a precise rate. In one embodiment for repairing burns, the target area with the burned skin is secured or fixed to avoid movement. The syringe pump is mounted above the area and deposits tissue and/or continuously administer analgesics (painkillers), antiemetics (medication to suppress nausea and vomiting) and other drugs. This prevents periods during which medication levels in the blood are too high or too low, and avoids the use of multiple tablets (especially in people who have difficulty swallowing). As the medication is administered subcutaneously, the area for administration is practically limitless, although edema may interfere with the action of some drugs.

The deposit nozzle 205 is coupled to a pen down sensor 213, such as a pressure sensitive element. In an alternate embodiment, the deposit nozzle 205 may make electronic marks on a biological surface 105 using a paired projector or electronic display.

The imaging system 210 comprises optics and sensors for imaging an area of a surface near the deposit nozzle 205. The imaging system 210 may be used to automatically detect boundaries of objects for deposition of biological materials thereon. For example, for skin reconstruction, the burned area is captured by the imaging system 210 and when a user scans the burned area, the imaging system 210 would instruct the 3D printer nozzle 205 to deposit materials only over the burned area. In other examples, to reconstruct an ear, the imaging system 210 would deposit the materials only over the appropriate regions to form the ear. In this manner, medical operations can be done in remote regions without hospitals, for example. In addition, the camera can capture handwriting and gestures made with the 3D printer pen 110. In yet other embodiments, the imaging system 210 may include a heat source or light source that heats or illuminates a biological surface 105 in the general vicinity of the deposit nozzle 205. By processing the image of the encoded pattern, the 3D printer pen 110 can determine where the deposit nozzle 205 is in relation to the biological surface 105.

The pen down sensor 213 determines when the smart pen is down. As used herein, the phrase "pen is down" indicates that the deposit nozzle 205 is pressed against or engaged with a biological surface 105. In an embodiment, the pen down sensor 213 produces an output when the pen is down, thereby detecting when the 3D printer pen 110 is being used to write on a surface or is being used to interact with controls or buttons (e.g., tapping) on a control paper. Embodiments of the pen down sensor 213 may include capacitive sensors, piezoresistive sensors, mechanical diaphragms, and electromagnetic diaphragms. The imaging system 210 may further be used in combination with the pen down sensor 213 to determine when the deposit nozzle 205 is touching the biological surface 105. For example, the imaging system 210 could be used to determine if the deposit nozzle 205 is within a particular range of a biological surface 105 using image processing (e.g. based on a fast Fourier transform of a capture image). In an alternate embodiment, a separate range-finding optical, laser, or acoustic device could be used with the pen down sensor 213. In an alternative embodiment, the 3D printer pen 110 can detect vibrations indicating when the pen is writing or interacting with controls on the biological surface 105. In an alternative embodiment, a pen up sensor may be used to determine when the 3D printer pen 110 is up. As used herein, the phrase "pen is up," indicates that the deposit nozzle 205 is neither pressed against nor engaged with a biological surface 105. In some embodiments, the pen down sensor 213 may additionally be coupled with the stylus tip 217, or there may be an additional pen down sensor coupled with or incorporated in the tip 217.

The power status mechanism 215 can toggle the power status of the smart pen 110. The power status mechanism may also sense and output the power status of the smart pen 110. The power status mechanism may be embodied as a rotatable switch integrated with the pen body, a mechanical button, a dial, a touch screen input, a capacitive button, an optical sensor, a temperature sensor, or a vibration sensor. When the power status mechanism 215 is toggled on, the pen's battery 235 is activated, as are the imaging system 210, the input/output device 220, the processor 225, and onboard memory 230. In some embodiments, the power status mechanism 215 toggles status lights, displays, microphones, speakers, and other components of the smart pen 110. In some embodiments, the power status mechanism 215 may be mechanically, electrically, or magnetically coupled to the deposit nozzle 205 such that the deposit nozzle 205 extends when the power status mechanism 215 is toggled on and retracts when the power status mechanism 215 is toggled off. In some embodiments, the power status mechanism 215 is coupled to the deposit nozzle 205 and/or the capacitive tip such that use of the marker and/or capacitive tip 217 toggles the power status. In some embodiments, the power status mechanism 215 may have multiple positions, each position toggling a particular subset of the components in the smart pen 110.

The tip 217 is used to write on or otherwise interact with devices or objects without leaving a physical ink mark. Examples of devices for use with the stylus tip might include tablets, phones, personal digital assistants, interactive whiteboards, or other devices capable of touch-sensitive input. The stylus tip may make use of capacitance or pressure sensing. In some embodiments, the stylus tip may be used in place of or in combination with the deposit nozzle 205.

The input/output (I/O) device 220 allows communication between the 3D printer pen 110 and the network 120 and/or the computing device 115. The I/O device 220 may include a wired and/or a wireless communication interface such as, for example, a Bluetooth, Wi-Fi, WiMax, 3G, 4G, infrared, or ultrasonic interface, as well as any supporting antennas and electronics.

A processor 225, onboard memory 230 (i.e., a non-transitory computer-readable storage medium), and battery 235 (or any other suitable power source) enable computing functionalities to be performed on the smart pen 110. The processor 225 is coupled to the input and output devices (e.g., imaging system 210, pen down sensor 213, power status mechanism 215, stylus tip 217, and input/output device 220) as well as onboard memory 230 and battery 235, thereby enabling applications running on the 3D printer pen 110 to use those components. As a result, executable applications can be stored to a non-transitory computer-readable storage medium of the onboard memory 230 and executed by the processor 225 to carry out the various functions attributed to the 3D printer pen 110 that are described herein. The memory 230 may furthermore store the recorded written and contextual data, either indefinitely or until offloaded from the 3D printer pen 110 to a computing system 115 or cloud server 125.

In an embodiment, the processor 225 and onboard memory 230 include one or more executable applications supporting and enabling a menu structure and navigation through a file system or application menu, allowing launch of an application or of a functionality of an application. For example, navigation between menu items comprises an interaction between the user and the 3D printer pen 110 involving spoken and/or written commands and/or gestures by the user and audio and/or visual feedback from the smart pen computing system. In an embodiment, pen commands can be activated using a "launch line." For example, on dot paper, the user draws a horizontal line from right to left and then back over the first segment, at which time the pen prompts the user for a command. The user then prints (e.g., using block characters) above the line the desired command or menu to be accessed (e.g., Wi-Fi Settings, Playback Recording, etc.). Using integrated character recognition (ICR), the pen can convert the written gestures into text for command or data input. In alternative embodiments, a different type of gesture can be recognized to enable the launch line. Hence, the 3D printer pen 110 may receive input to navigate the menu structure from a variety of modalities.

During a smart pen computing session, the pen-based computing system 100 acquires content that comes in two primary forms, that generated or collected through the operation of the smart pen 110, and that generated in or collected by a computing device 115. This data may include, for example, stroke data, audio data, digital content data, and other contextual data.

Figure 4:
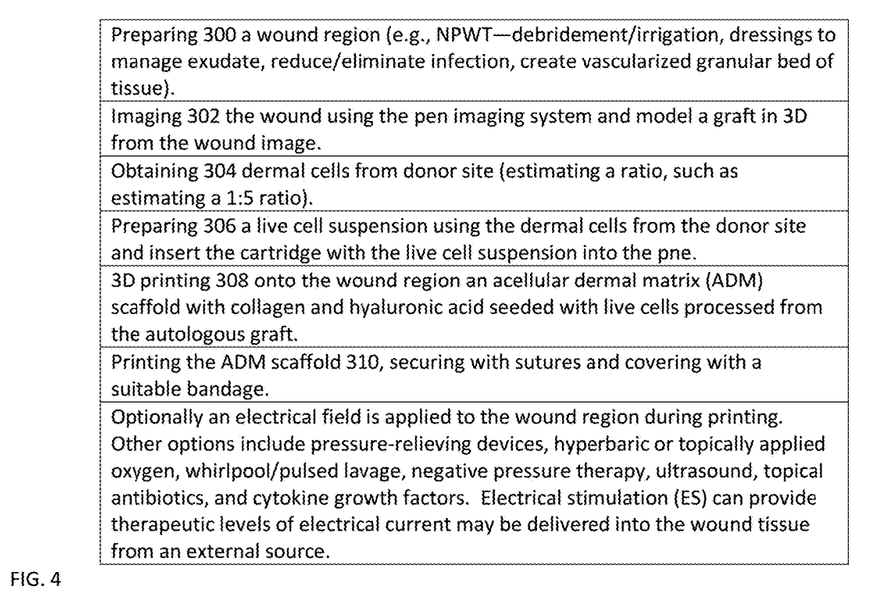
FIG. 4 shows an exemplary process for 3D printing and repairing burned skin.

As may be further appreciated with reference to FIG. 4, an example of a skin printing process includes:

Preparing 300 a wound region (e.g., NPWT—debridement/irrigation, dressings to manage exudate, reduce/eliminate infection, create vascularized granular bed of tissue).

Imaging 302 the wound using the pen imaging system and model a graft in 3D from the wound image.

Obtaining 304 dermal cells from donor site (estimating a ratio, such as estimating a 1:5 ratio).

Preparing 306 a live cell suspension using the dermal cells from the donor site and insert the cartridge with the live cell suspension into the one.

3D printing 308 onto the wound region an acellular dermal matrix (ADM) scaffold with collagen and hyaluronic acid seeded with live cells processed from the autologous graft.

Printing the ADM scaffold 310, securing with sutures and covering with a suitable bandage.

Optionally an electrical field is applied to the wound region during printing. Other options include pressure-relieving devices, hyperbaric or topically applied oxygen, whirlpool/pulsed lavage, negative pressure therapy, ultrasound, topical antibiotics, and cytokine growth factors. Electrical stimulation (ES) can provide therapeutic levels of electrical current may be delivered into the wound tissue from an external source. The external current may serve to mimic the failed natural bioelectric currents so that wound healing can proceed. Certain chemotaxic factors found in wound substrates contribute to tissue repair processes by attracting cells into the wound environment. Neutrophil, macrophage, fibroblast, and epidermal cells involved in wound repair carry either a positive or negative charge. When these cells are needed to contribute to autolysis, granulation tissue formation, anti-inflammatory activities, or epidermal resurfacing, ES may facilitate galvanotaxic attraction of these cells into the wound tissue and thereby accelerate healing.

In one implementations, surgical instrument is used to separate epidermis from skin at a donor site preferably of a same patient who has wound. Separated epidermis is processed by enzymatic cell separation to produce separated dermal cells which are dissolved to produce a dermal cell solution. Dermal cell solution is cultured onto plates to provide plated dermal cells and/or is split into dermal cell solutions (such as 70% confluency). Cultured dermal cells and dermal cell solutions are harvested, to be transferred to 3D printer cell dispensers such as dispenser. Following harvest of the donor site, individual cells of the epidermal layer are dissociated from the dermis. Dissociation of skin cells is accomplished by traditional trypsin: EDTA methods which is a preferable method for isolating keratinocytes from human skin. Human serum, bovine serum albumin, serum fibronectin, type IV collagen, and laminin are added to traditional cell culture media provide support to the fibroblasts and keratinocytes. These basement membrane protein constituents form the layers of the extracellular matrix on which these epidermal and dermal cells grow. Disassociated cells are incubated and continually shaken in cell culture flasks at 37° C. Cells are sub-cultured prior to confluency and allowed either to continue to proliferate in dissociated cell suspension flasks, plated on collagen plates to continue growth, or plated via the skin printer onto bovine collagen substrates.

In one embodiment, a bovine collagen matrix is augmented with growth factors such as Platelet-Derived Growth Factor (PDGF), epidermal Nitric Oxide Synthase (eNOS), Vascular Endothelial Growth Factor (VEGF), and Tumor Necrosis Factor Beta (TNF-beta). Low-dose insulin is added to also promote cell growth and proliferation. Insulin is used to improve wound healing and may be beneficial when used in an in vitro model to increase cell proliferation and would enhance cell proliferation into the collagen matrix.

3-4 days following the first application of autologous cells, and as the allogeneic cells and matrix begin to form obvious healthy epithelial tissue, lyophilized amniotic membrane (AM) is sprayed (such as from a modified airbrush-like apparatus (preferably associated with the print head of the 3D printer) onto the cell-seeded bovine collagen. There is a notable body of evidence to suggest that freeze-dried, powdered amniotic membrane promotes rapid healing and enhances the "take" rate of grafts. AM also inhibits natural inflammatory reactions which contribute to healthy tissue adhesion and structural development. There is evidence to suggest that combined with an electrical field, the application of AM will enhance cell migration and angiogenesis to cells located in the center-most region of the graft bed.

Continual layers of the cultured material are printed onto collagen plates until desired thickness is achieved. Amount of cells wanted in each layer, number of times the printer must create layers for the skin graft, intervals between applications, and types and amounts of growth factors and other ECM proteins to be added are factors.

As biofabricated hydrogel constructs for implantation usually have a lower stiffness than their target tissue, especially for use in the musculoskeletal system, improving stiffness of the hydrogel itself could be achieved by increasing the hydrogel crosslink density. In order to combine favorable biological and mechanical hydrogel properties, reinforcement of hydrogels has been achieved at different levels. Hydrogels have been reinforced by use of double networks and interpenetrating polymer networks (IPN), as well as by incorporation of nanoparticles, nanotubes or electrospun fibers. The crosslink density of the hydrogel could remain relatively low allowing for adequate tissue formation. However, most of these approaches will not be compatible with AM processes, since fabrication requires casting or a two-step crosslinking reaction. Therefore, recently multiple-tool biofabrication has been developed in which hydrogel constructs are reinforced by co-deposited thermoplastic polymer fibers by combining hydrogel and PCL in robotic dispensing and by combining electrospinning techniques with inkjet printing or laser-induced forward transfer printing. In this way, hydrogels can be processed at low polymer concentrations while shape and strength of the overall construct are secured by the thermoplastic polymer network. Moreover, it can be used in order to fabricate more complex shaped tissue constructs and the Young's modulus of the target construct can be tailored by adjusting the thermoplastic polymer network. Electrospinning produces a higher resolution of PCL fibers compared to robotic dispensing, and results in a network that better approaches the structure of natural ECM. Combining this technique with hydrogel deposition approaches will allow for the generation of reinforced hydrogel constructs with high control over the intricate spatial organization, although grafting between fibers and the hydrogel needs to be addressed in order to biofabricate truly integrated constructs. In addition, degradation kinetics of these hybrid structures should be understood and controlled. The hydrogel scaffold acts as a temporary environment and degrades as the embedded cells secrete proteases and subsequently produce extracellular matrix proteins that define the new tissue. In contrast, the polymeric reinforcement material should degrade in a significant slower rate, providing strength to the developing construct until the tissue has matured and at least once remodeled.

In one embodiment, photocrosslinkable interpenetrating polymeric network (IPN) of collagen and hyaluronic acid (HA) with precisely controlled structural and biomechanical properties. Both collagen and HA are present in crosslinked form in IPNs, and the two networks are entangled with each other. IPNs were also compared with semi-IPNs (SIPN), in which only collagen was in network form and HA chains were entangled in the collagen network without being photocrosslinked. Scanning electron microscopy images revealed that IPNs are denser than SIPNs, which results in their molecular reinforcement. This was further confirmed by rheological experiments. Because of the presence of the HA crosslinked network, the storage modulus of IPNs was almost two orders of magnitude higher than SIPNs. The degradation of the collagen-HA IPNs was slower than the SIPNs because of the presence of the crosslinked HA network. Increasing concentration of HA further altered the properties among IPNs. Cytocompatibility of IPNs was confirmed by Schwann cell and dermal fibroblasts adhesion and proliferation studies. We also fabricated patterned scaffolds with regions of IPNs and SIPNs within a bulk hydrogel, resulting in zonal distribution of crosslinking densities, viscoelasticities, water content and pore sizes at the micro- and macro-scales.

The pen can be used in the following exemplary applications:

Skin. In representative embodiments, to produce epidermal-like skin tissue, the following are printed:
  (a) at least one cell type, and preferably at least two or in some embodiments three or four different epidermal cell types (e.g., keratinocytes, melanocytes, Merkel cells, Langerhan cells, etc., and any combination thereof); and/or
  (b) at least one support compound such as described above (e.g., collagen, hyaluronic acid, elastin, keratin, etc., and any combination thereof); and/or
  (c) at least one growth factor as described above (e.g., basic fibroblast growth factor (bFGF), Insulin-Like Growth Factor 1, epidermal growth factor (EGF), etc., and any combination thereof);
In some embodiments the epidermal cells, support compound and/or growth factors printed as described above (which form an "epidermal" type layer) are printed on, or on top of, a previously formed (e.g., printed or ink-jet printed) "dermal" type layer, the previously printed dermal layer layers comprising: (a) one, two, three or four different dermal cells (fibroblasts, adipocytes, mast cells, and/or macrophages), (b) at least one support compound as described above; and/or (c) at least one growth factor as described above.

Skin tissue produced by the method of the present invention is useful for implantation into or on a subject to, for example, treat burns, and other wounds such as incisions, lacerations, and crush injuries (e.g., postsurgical wounds, and posttraumatic wounds, venous leg ulcers, diabetic foot ulcers, etc.)

Bone. In particular embodiments, to produce bone tissues, the following are printed:

(a) at least one bone cell type, and preferably at least two or three different bone cell types (e.g., osteoblasts, osteoclasts, osteocytes, and any combination thereof, but in some embodiments at least osteoblasts and osteoclasts, and in some embodiments all three); and/or (b) at least one support compound such as described above (e.g., collagen, hyaluronic acid, hydroxyapatites, calicite, silica, ceramic, proteoglycans, glycoproteins, etc., and any combination thereof); and/or (c) at least one growth factor (e.g., bone morphogenetic protein, transforming growth factor, fibroblast growth factors, platelet-derived growth factors, insulin-like growth factors, etc., and any combination thereof).

Bone tissues produced by the processes described herein are useful for, among other things, implantation into a subject to treat bone fractures or defects, and/or promote bone healing.

Pancreatic. In representative embodiments, to produce pancreatic islet tissues, the following are printed:

(a) at least one, two, or three different pancreatic islet cell type (e.g., glucagon-synthesizing A (α) cells, insulin-producing B (β) cells, D (δ) cells, etc., and any combination thereof); and/or (b) at least one support compound such as described above (e.g., collagen, hyaluronic acid, proteoglycans, glycoproteins, elastin, etc., and any combination thereof); and/or (c) at least one growth factor (e.g., insulin-Like Growth Factor II (IGF-II), gastrin, transforming growth factor-alpha (TGF alpha), vascular endothelial growth factor (VEGF), etc., and any combination thereof)

Pancreatic islet tissue produced by the processes described herein is useful for, among other things, implantation into a subject to treat diabetes (including type I and type II diabetes).

Nerve. In representative embodiments, to produce nerve tissue, the following are printed:

(a) at least one, two or three cells types, and preferably (i) a central or peripheral nerve cells (e.g., cortical neurons, hippocampal neurons, dopaminergic neurons, cholinergic neurons, adrenergic neurons, noradrenergic neurons, etc., including any combination thererof), and/or (ii) at least one glial cell type (e.g., neuroglia, astrocytes, oligodendrocytes, Schwann cells, etc., including any combination thereof) and (iii) any combination thereof (e.g. a combination of at least one nerve cell and at least one glial cell); and/or (b) at least one support compound such as described above; (e.g., laminin, hyaluronic acid, collagen type IV, fibronectin, etc., and any combination thereof); and/or (c) at least one growth factor (e.g., NGF, brain-derived neurotrophic factor, insulin-like growth factor-I, fibroblast growth factor, etc., or any combination thereof); and any combination of the foregoing.

Nerve tissue produced by the processes described herein is useful, among other things, for implantation into a subject to treat nerve injury or degenerative diseases such as Parkinson's disease and Alzheimer's disease.

In some embodiments stem cells are printed onto substrates by ink-jet printing. Stem cells may be printed alone (typically in combination with a support compound or compounds) or in combination with one or more additional cells (e.g. in a combination selected to produce a tissue as described above). Stem cells (such as pluripotent or multipotent cells) are capable of differentiating into multiple different cell types or lines, including at least one of a hepatogenic-specific (or liver-specific) cell line, a myogenic (or muscle specific) cell line, an osteogenic (or bone specific) cell line, or an endothelial specific cell line. Useful cells for carrying out the invention include but are not limited to embryonic stem cells, parthenogenetic stem cells, amniotic fluid stem cells, and adipose-derived stem cells.

In general, AFSCs are cells, or progeny of cells, that are found in or collected primarily from mammalian amniotic fluid, but may also be collected from mammalian chorionic villus or mammalian placental tissue. The cells are preferably collected during the second trimester of gestation. In mice the cells are most preferably collected during days 11 and 12 of gestation. Preferably the mammalian source is of the same species as the mammalian subject being treated.

In general, the tissue or fluid can be withdrawn by amniocentesis, punch-biopsy, homogenizing the placenta or a portion thereof, or other tissue sampling techniques, in accordance with known techniques. From the sample, stem cells or pluripotent cells may be isolated with the use of a particular marker or selection antibody that specifically binds stem cells, in accordance with known techniques such as affinity binding and/or cell sorting. AFSCs used to carry out the present invention are pluripotent. Hence, they differentiate, upon appropriate stimulation, into at least osteogenic, adipogenic, myogenic, neurogenic, hematopoitic, and endothelial cells. Appropriate stimulation, for example, may be as follows: Osteogenic induction: The cKit+ cells are cultured in DMEM low glucose with 10% FBS supplementing with 100 nM dexamethasone (Sigma-Aldrich), 10 mM beta-glycerophosphate (Sigma-Aldrich) and 0.05 mM ascorbic acid-2-phosphate (Wako Chemicals, Irving, Tex.); Adipogenic induction: To promote adipogenic differentiation, c-Kit+ cells are seeded at density of 3000 cells/cm2 in DMEN low glucose medium with 10% FBS supplemented with 1 μM dexamethasone, 1 mM 3-isobutyl-1-methylxantine, 10 μg/ml insulin and 60 μM indomethacin (all from Sigma-Aldrich); Myogenic induction: c-Kit+ cells were plated into Matrigel-precoated dish (1 mg/ml, Collaborative Biomedical Products) and cultured in myogenic medium (DMEM low glucose supplemented with 10% horse serum, and 0.5% chick embryo extract from Gibco) followed by treatment of 5 azacytidine (10 μM, Sigma) added in myogenic medium for 24 h; Endothelial induction: c-Kit+ cells are plated into gelatin-precoated dish and cultured in endothelial basal medium-2 (EBM-2, Clonetics BioWittaker) supplemented with 10% FBS and 1% glutamine (Gibco). In preferred embodiments no feeder layer or leukaemia inhibitory factor (LIF) are required either for expansion or maintenance of AFSCs in the entire culture process.

AFSCs also have substantial proliferative potential. For example, they proliferate through at least 60 or 80 population doublings or more when grown in vitro. In preferred embodiments AFSCs used to carry out the invention proliferate through 100, 200 or 300 population doublings or more when grown in vitro. In vitro growth conditions for such determinations may be: (a) placing of the amniotic fluid or other crude cell-containing fraction from the mammalian source onto a 24 well Petri dish containing a culture medium [α-MEM (Gibco) containing 15% ES-FBS, 1% glutamine and 1% Pen/Strept from Gibco supplemented with 18% Chang B and 2% Chang C from Irvine Scientific], upon which the cells are grown to confluence, (b) dissociating the cells by 0.05% trypsin/EDTA (Gibco), (c) isolating an AFSC subpopulation based on expression of a cell marker c-Kit using mini-MACS (Mitenyl Biotec Inc.), (d) plating of cells onto a Petri dish at a density of 3-8×103/cm2, and (e) maintaining the cells in culture medium for more than the desired time or number of population doublings.

Preferably, the AFSCs are also characterized by the ability to be grown in vitro without the need for feeder cells (as described in PCT Application WO 03/042405 to Atala and DeCoppi. In preferred embodiments undifferentiated AFSCs stop proliferating when grown to confluence in vivo.

AFSCs used to carry out the present invention are preferably positive for alkaline phosphatase, preferably positive for Thy-1, and preferably positive for Oct4, all of which are known markers for embryonic stem cells, and all of which can be detected in accordance with known techniques. See, e.g., Rossant, J., Stem cells from the Mammalian blastocyst. Stem Cells, 2001. 19(6): p. 477-82; Prusa, A. R., et al., Oct-4-expressing cells in human amniotic fluid; a new source for stem cell research? Hum Reprod, 2003. 18(7): p. 1489-93.

In a particularly preferred embodiment, the AFSCs do not form a teratoma when undiferentiated AFSCs are grown in vivo. For example, undifferentiated AFSCs do not form a teratoma within one or two months after intraarterial injection into a 6-8 week old mouse at a dose of 5×106 cells per mouse.

In preferred embodiments the amniotic fluid stem cells used to carry out the present invention express several markers characteristic of ES cells and/or various multipotent adult stem cells. These include the transcription factor Oct-4 (Pou5f1), SSEA-1 (Stage Specific Embryonic Antigen 1), Sca-1 (Ly-6A/E), CD90 (Thy-1), and CD44 (Hyaluronate receptor. Ly-24, Pgp-1).

In preferred embodiments the amniotic fluid stem cells used to carry out the present invention do not express CD34 and CD105, markers of certain lineage restricted progenitors, nor the hematopoietic marker CD45.

In preferred embodiments the amniotic fluid stem cells used to carry out the present invention express low levels of major histocompatibility (MHC) Class I antigens and are negative for MHC Class II.

Differentiation of cells. "Differentiation" and "differentiating" as used herein include (a) treatment of the cells to induce differentiation and completion of differentiation of the cells in response to such treatment, both prior to printing on a substrate, (b) treatment of the cells to induce differentiation, then printing of the cells on a substrate, and then differentiation of the cells in response to such treatment after they have been printed, (c) printing of the cells, simultaneously or sequentially, with a differentiation factor(s) that induces differentiation after the cells have been printed, (d) contacting the cells after printing to differentiation factors or media, etc., and combinations of all of the foregoing. In some embodiments differentiation may be modulated or delayed by contacting an appropriate factor or factors to the cell in like manner as described above. In some embodiments appropriate differentiation factors are one or more of the growth factors described above. Differentiation and modulation of differentiation can be carried out in accordance with known techniques or variations of the above or below that will be apparent to those skilled in the art.

Pancreas. Differentiation of cells to pancreatic-like cells can be carried out in accordance with any of a variety of known techniques. For example, the cells can be contacted to, printed with, or cultured in a conditioning media Osteogenic induction: Cells may be induced to form bone cells by any suitable technique, such as culturing in DMEN low glucose with 10% FBS supplementing with 100 nM dexamethasone (Sigma-Aldrich), 10 mM beta-glycerophosphate (Sigma-Aldrich) and 0.05 mM ascorbic acid-2-phosphate (Wako Chemicals, Irving, Tex.).

Adipogenic induction: Cells may be induced to promote adipogenic differentiation by any suitable technique, such as culturing in DMEN low glucose medium with 10% FBS supplemented with 1 µM dexamethasone, 1 mM 3-isobutyl-1-methylxantine, 10 µg/ml insulin and 60 µM indomethacin (all from Sigma-Aldrich);

Myogenic induction: Cells may be induced to promote myogenic induction by any suitable technique, such as culturing in myogenic medium (DMEM low glucose supplemented with 10% horse serum, and 0.5% chick embryo extract from Gibco) followed by treatment of 5-azacytidine (10 µM, Sigma) added in myogenic medium for 24 h.

Endothelial induction: Cells may be induced to promote endothelial induction by any suitable technique, such as culturing in endothelial basal medium-2 (EBM-2, Clonetics BioWittaker) supplemented with 10% FBS and 1% glutamine (Gibco).

Figure 5:
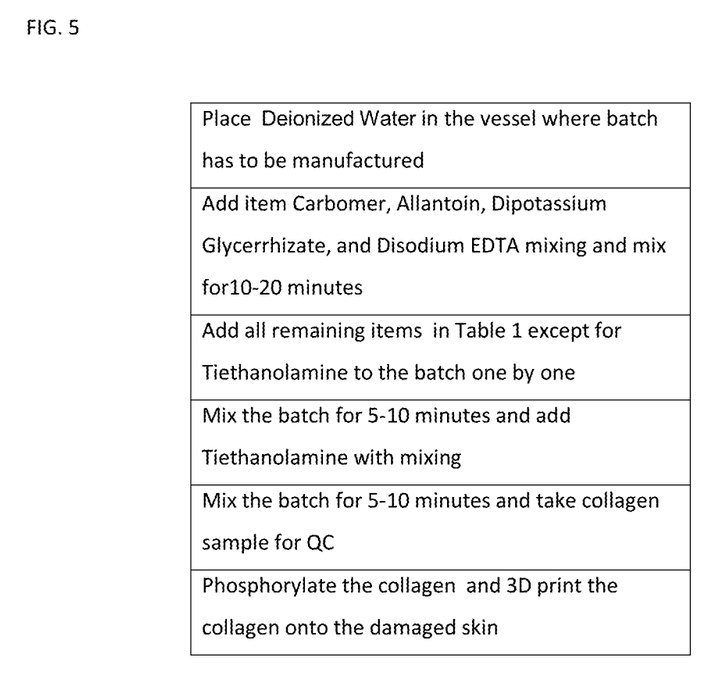
FIG. 5 shows an exemplary process of applying collagen to repair tissue.

In another aspect, a collagen solution suitable for 3D printing onto the damaged skin is detailed. FIG. 5 shows an exemplary process for forming a wound healing solution. First, in 100, Deionized Water is placed in a vessel where batch has to be manufactured. Next, in 102, Carbomer, Allantoin, Dipotassium Glycerrhizate, and Disodium EDTA are added and mixed for 10-20 minutes. In 103, the remaining items in Table 1, except for Tiethanolamine, are added to the batch one by one. In 104, the batch is mixed for 5-10 minutes and Tiethanolamine is added with mixing. In 105, the batch is mixed for 5-10 minutes and the resulting collagen sample(s) can be taken for QC. Next, collagen is preferably phosphorylated with PX3 Phosphorus (Orthophosphoric Acid) which has the best binding capability to the collagen and shows the best results for the wound healing process. Phosphorylation is the metabolic process of introducing a phosphate group into the collagen's organic molecule. Orthophosphoric acid is the optimum material for different types of collagen in a controlled environment. Orthophosphoric acid is an inorganic acid. It is also known as phosphoric acid. The chemical structure of orthophosphoric acid is $H_3PO_4$, but these molecules can be re-combined to produce a number of compounds. Any derivatives of this acid are also referred to as phosphoric acids. The pure form of this acid is solid and white at room temperature. At 108.23° F. (42.35° C.), orthophosphoric acid will melt, resulting in a viscous, colorless liquid. At room temperature, this compound is typically anhydrous, which means it does not contain water. It has a polar molecular structure, however, which means that it is extremely soluble in water. As a chemical reagent, this acid is often converted into aqueous, or water-containing, solutions. These can have a potentiometric hydrogen ion concentrations (pH) ranging from 1.08 to 7.00, depending on the amount of acid present. An 85% solution of orthophosphoric acid is corrosive, but can be made non-toxic by way of dilution. Phosphate is a major intracellular anion which participates in providing energy for metabolism of substances and contributes to important metabolic and enzymatic reactions in almost all organs and tissues. Phosphate exerts a modifying influence on calcium concentrations, a buffering effect on acid-base equilibrium, and has a major role in the renal excretion of hydrogen ions.

Advantages of the composition and method for improving wound healing by administering either systemically or locally a therapeutic composition comprising phosphorylated collagen may include one or more of the following. The method provides for improved wound healing time, as well as a reduction in scar tissue formation and reduced loss of tissue function. The method will be particularly useful in cosmetic treatment have been shown here to increase the rate of wound healing by acceleration and enhancement of several key processes. The application of phosphorylated collagen has also been shown to result in decreased deposition of collagen at the final healed wound site which prevents loss of tissue function (strength) or cosmetic damage due to scarring.

The solution uses ingredients in Table 1 below:

| Item | Ingredients | Purpose & Usage | % w/w |
|---|---|---|---|
| 1 | Deionized Water (Aqua) | Solvent | 61.05 |
| 2 | Sodium Hyaluronate | Moisturizing | 7.50 |
| 3 | Propylene Glycol & t Camellia Oleifera Leaf Extrac | Conditioning | 7.00 |
| 4 | Butylene Glycol | Humectant | 5.00 |
| 5 | Polysorbate 20 | Solubilizer | 3.50 |
| 6 | Propylene Glycol & Spiraea Ulmaria Flower Extract & Centella Asiatica Extract & Amino Acids | Conditioning | 2.50 |
| 7 | PEG-8 Dimethicone | Conditioning | 2.50 |
| 8 | Water & Imperata cylindrica Root Extract & Glycerin & PEG-8 & Carbomer | Conditioning | 2.00 |
| 9 | Collagen | Antiaging | 1.00 |
| 10 | Aloe Barbadensis Leaf Extract | Soothing | 1.00 |
| 11 | Carbomer | Viscosity Builder | 1.00 |
| 12 | Panthenol (Provitamin B5) | Conditioning | 1.00 |
| 13 | Water (Aqua) & Crithmum maritimum extract | Conditioning | 1.00 |
| 14 | Algae Extract & Mugwort (Artemisia Vulgaris) Extract | Conditioning | 1.00 |
| 15 | Phenoxyethanol-Methylparaben-Ethylparaben-n-Propylparaben-n-Butylparaben-iso-Butylparaben | Preservative | 1.00 |
| 16 | Sodium Ascorbyl Phosphate (Vitamin C) | Antioxidant | 1.00 |
| 17 | Triethanolamine | pH Adjuster | 0.50 |
| 18 | Water & Copper PCA & L-tyrosine & Glycine | Conditioning | 0.20 |
| 19 | Allantoin | Conditioning | 0.10 |
| 20 | Dipotassium Glycyrrhizate | Conditioning | 0.10 |
| 21 | Disodium EDTA | Chelating Agent | 0.05 |

While preferred embodiments have been described above and illustrated in the accompanying drawings, it will be evident to those skilled in the art that modifications may be made without departing from this disclosure. Such modifications are considered as possible variants comprised in the scope of the disclosure.

What is claimed is:

1. A method of healing a skin wound, comprising:
    obtaining dermal cells from a donor site and preparing a live cell suspension using the dermal cells from a donor site;
    inserting a supply cartridge with the live cell suspension into a pen;
    imaging the skin wound using an imager;
    printing onto the skin wound an acellular dermal matrix (ADM) scaffold with collagen and seeded with live cells processed from the autologous graft, wherein a processor determines a boundary of the skin wound through image processing, detects positional information of the pen, and selectively prints over the skin wound; and
    securing with sutures and covering with a bandage.

2. The method of claim 1, comprising 3d printing a three-dimensional irregularly-shaped object.

3. The method of claim 1, comprising printing a quantity of harvested skin cells.

4. The method of claim 1, comprising wherein the scaffold comprises a photocrosslinkable interpenetrating polymeric network (IPN) of collagen and hyaluronic acid (HA).

5. The method of claim 1, comprising surgically implanting an object into a living subject, where the cells continue to live in the living subject.

6. The method of claim 1, comprising printing materials with nerve tissues.

7. The method of claim 1, comprising printing materials with stem cells.

8. The method of claim 1, comprising injecting one or more bio-materials using a syringe in the pen or spraying a mist of the one or more bio-materials using a MEMS actuator.

9. The method of claim 1, comprising transmitting a target area image to a remote medical professional.

* * * * *